United States Patent [19]

Argoudelis et al.

[11] 4,383,109

[45] May 10, 1983

[54] LINCOMYCIN NUCLEOTIDES

[75] Inventors: Alexander D. Argoudelis; David W. Stroman, both of Portage, Mich.

[73] Assignee: The Upjohn Company, Kalamazoo, Mich.

[21] Appl. No.: 255,542

[22] Filed: Apr. 20, 1981

[51] Int. Cl.³ .................... C07H 15/16; C12P 19/30; C12P 19/32
[52] U.S. Cl. .................................. 536/16.5; 424/180; 536/16.2; 435/92
[58] Field of Search ...................... 536/11, 16.2, 16.5

[56] References Cited

U.S. PATENT DOCUMENTS

| | | | |
|---|---|---|---|
| 3,086,912 | 4/1963 | Bergy et al. | 536/16.2 |
| 3,496,163 | 2/1970 | Birkenmeyer et al. | 536/16.2 |
| 3,671,647 | 6/1972 | Argoudelis et al. | 536/16.5 |
| 4,278,789 | 7/1981 | Birkenmeyer | 536/11 |
| 4,309,533 | 1/1982 | Birkenmeyer | 536/11 |
| 4,310,660 | 1/1982 | Birkenmeyer | 536/11 |

*Primary Examiner*—Johnnie R. Brown
*Attorney, Agent, or Firm*—Roman Saliwanchik

[57] ABSTRACT

Novel and useful ribonucleotides of analogs of the well known antibiotics lincomycin and clindamycin. These ribonucleotides are unexpectedly highly active against *Streptococcus hemolyticus* and *Staphylococcus aureus* in vivo.

29 Claims, No Drawings

LINCOMYCIN NUCLEOTIDES

BACKGROUND OF THE INVENTION

The characteristics and preparation of the antibiotic lincomycin are disclosed in U.S. Pat. No. 3,086,912. Clindamycin is disclosed in U.S. Pat. No. 3,496,163. These antibiotics have been extensively used as medicines in humans and animals. A number of patents world-wide have issued concerning these antibiotics and a variety of derivatives thereof.

The structural formulas for lincomycin (1) and clindamycin (2) are shown in Chart 1.

Linomycin and clindamycin 3-nucleotides are disclosed and claimed in U.S. Pat. No. 3,671,647. All of the lincomycin and clindamycin compounds disclosed in U.S. Pat. No. 3,671,647 have the propyl hygric acid moiety. These 3-nucleotides were found by test against *S. aureus in vivo* to have an activity approximately one-tenth of the parent compound.

BRIEF SUMMARY OF THE INVENTION

The subject invention concerns the 3-ribonucleotides of lincomycin- and clindamycin-type compounds in which the propyl hygric acid moiety has been replaced by different cyclic amino acids. Unexpectedly, these nucleotides demonstrate in vivo antibacterial activity as high as the parent compounds. Because of these highly relevant characteristics, the nucleotides of the subject invention are considered to be prime candidates for medicinal use.

The lincomycin- and clindamycin-type compounds which can be converted to the 3-ribonucleotides are shown in Chart 2. In place of the hydroxyl at the three position of the lincosaminide moiety, there is substituted a nucleotide selected from the group consisting of adenylic acid, guanylic acid, cytidylic acid and uridylic acid.

The 3-ribonucleotides of the subject invention can be prepared by microbiological transformation procedures. The 3-(5'-ribonucleotides) obtained by transformation of U-57930 are shown in Chart 3.

DETAILED DESCRIPTION

The parent compounds disclosed in Chart 2 can be prepared by the procedures disclosed in pending U.S. patent application Ser. No. 148,056, now U.S. Pat. No. 4,278,789.

The 3-(5'-ribonucleotides) of the compounds of Chart 2 can be prepared by following the procedures disclosed in U.S. Pat. No. 3,671,647. Salts of these nucleotides also can be prepared following the procedures in U.S. Pat. No. 3,671,647.

Formulations of the nucleotides of this invention can be made following the composition examples in U.S. Pat. No. 4,278,789 148,056. The formulations are prepared by substituting a nucleotide of the subject invention for the active compound in the examples. The substitution can be on an equimolar basis.

General assay and characterization procedures which can be employed to determine and characterize the nucleotides of the invention are as follows:

Assay of 3-(5'-Ribonucleotides)

Since the 3-ribonucleotides of this invention lack in vitro antibacterial activity, their formation from the antibacterially-active parent compounds can be followed easily by measuring the loss of such antibiotic activity. To determine the amounts of antibacterially-active parent compound in culture filtrates or reaction mixtures, a standard assay with *Sarcina lutea* ATCC 9341 is employed. To assay for the presence of the 3-ribonucleotides in fermentation beers, extracts, and purified materials, the phosphodiester bond is first hydrolyzed with crude alkaline phosphatase, or snake venom phosphodiesterase, by the procedures described below. The antibacterially-active compound in the hydrolysate is determined by standard assay.

Enzymatic Hydrolyses

Alkaline Phosphatase: Stock solutions (0.5 mg/ml, 0.54 Units/mg) of pigeon intestine alkaline phosphatase, EC 3.1.3.1 (Sigma) are prepared in Tris (hydroxymethyl) aminomethane hydrochloride buffer, 0.01 M pH 8.0. Samples to be treated are diluted 1:2 with the enzyme buffer mixture and are incubated at 28° C. for 18 hours.

Snake Venom Phosphodiesterase: Stock solutions (100 mg/ml, 0.026 Units/mg) of purified snake venom phosphodiesterase EC 3.1.4.1 (Sigma) are prepared in distilled water. Incubation mixtures contain 0.2 ml of a solution (1 mg/ml) of the sample to be treated in water, 0.6 ml of 0.01 M Tris-hydrochloride buffer, pH 9.0, 0.1 ml of 0.3 M $MgCl_2$, and 0.1 ml of the enzyme stock solution. Incubation is carried out at 37° C. for 18 hours.

Spleen Phosphodiesterase: Stock solutions of spleen phosphodiesterase EC 3.1.4.18 (Sigma) are prepared (1 mg/ml, 19.6 Units/mg) in distilled water. Incubation mixtures contain 0.4 ml of a solution (0.5 mg/ml) of the sample to be treated in water, 0.5 ml of 0.02 M Tris buffer, pH 7.0 and 0.1 ml of the enzyme stock solution. Incubation is carried out at 37° C. for 18 hours.

Thin-Layer Chromatographic Analysis of Preparations and Enzymatic Hydrolysates The production and purification of the 3-ribonucleotides is followed by assay against *S. lutea* (see above) and by TLC using silica gel G and methyl ethyl ketone-acetone-water (186:52:20, v/v) or ethyl acetate-acetone-water (8:5:1) as the solvent systems. The bioactive parent compounds are detected by bioautography on agar seeded with *S. lutea*.

The products of enzymatic or chemical hydrolysis of the 3-nucleotides are separated by the following TLC systems:

A: Silica gel GF plates (Analtech Inc.); water as the solvent system.

B: Silica gel GF plates; n-propyl alcohol-conc. ammonium hydroxide-water (55:10:35, v/v).

C: NM-Polygram Cellulose 300 (Brinkman Instruments Inc.); 1-butanol-water-formic acid (77:13:10, v/v).

UV absorbing materials are detected by a short wavelength UV lamp. Bioinactive, UV-nonabsorbing materials are detected by a permanganate-periodate spray reagent. Bioactive nucleotide materials are detected by bioautography on agar seeded with *S. lutea*.

The following example shows the fermentation and purification procedures for preparing the nucleotide of the compound designated as U-57930E. The structural formula of U-57930E is shown in Chart 3. By following the procedures of this example, or obvious equivalents thereof, there can be made the 3-ribonucleotides of the other compounds disclosed in Chart 2.

The following example is illustrative of the process and products of the invention, but are not to be construed as limiting. All percentages are by weight and all solvent mixture proportions are by volume unless otherwise noted.

EXAMPLE 1

A. Fermentation Procedure

*Streptomyces rochei*, NRRL 3533, is grown in a medium consisting of glucose, 10 g/liter; Difco peptone, 4 g/liter; Difco yeast extract, 4 g/liter; $MgSO_4.7H_2O$, 0.5 g/liter; $KH_2PO_4$, 2.0 g/liter; $K_2HPO_4$, 4 g/liter for three days at 28° C. on a rotary shaker. The mycelium from this growth is used to inoculate a fermentation medium containing the same ingredients. The fermentation is carried out for 48 hours at 28° C. on a rotary shaker. At the end of this 48-hour incubation, U-57930 is added to a final concentration of 50 mg/liter and the fermentation continued at 32° C. After the twelve hours, additional U-57930 is added to make the total concentration 150 mg/liter. After twelve additional hours, the HU-57930 concentration is increased to 250 mg/liter. The fermentation is continued at 32° for 24 hours after the last addition of U-57930. At this time the culture filtrates are harvested and found to contain no more than 1 mg/liter of U-57930. The remaining 249 mg/liter is converted to bioinactive material.

*S. rochei*, NRRL 3533, is a known microbe which is available to the public upon request from the NRRL repository. The address of this repository is as follows: Northern Utilization and Research Division, Agricultural Research Service, U.S. Department of Agriculture, Peoria, Ill., U.S.A.

B. Isolation and Purification Procedures

Isolation of U-57930 3-Ribonucleotides from Fermentation Broth Adsorption on Amberlite XAD-2: Fermentation broth (ca 12 liter) containing 3 g of inactivated U-57930 is filtered at harvest pH (7.7) by using filter aid. The mycelial cake is washed with 1.2 liter of water and discarded. The clear filtrate and wash are combined and adjusted to pH 6.0 and passed over a column prepared from 600 ml of Amberlite XAD-2 (Rohm and Haas Co., Philadelphia, PA), at a flow rate of 40 ml/minute. The spent is tested for bioactivity before and after treatment with alkaline phosphatase and is discarded. The column is washed with 2 liters of water. The aqueous wash is also found bioinactive before and after treatment with alkaline phosphatase and is discarded. The column is then eluted with methanol-water (70:30 v/v). Fractions of 20 ml are collected at a rate of 20 ml/minute. Testing for bioactivity before (−E) and after (+E) treatment with alkaline phosphatase shows the following:

| Fraction No. | Zone (*S. lutea*) | |
| --- | --- | --- |
| | −E | +E |
| 5 | 0 | 0 |
| 10 | 0 | 0 |
| 11 | 0 | 0 |
| 13 | 0 | 36 |
| 20 | 33 | 55 |
| 25 | 32 | 54 |
| 40 | 31 | 50 |
| 45 | 29 | 48 |
| 50 | 26 | 39 |
| 55 | 23 | 38 |
| 60 | 21 | 37 |
| 65 | 19 | 27 |
| 70 | 17 | 26 |
| 75 | 17 | 26 |
| 80 | 16 | 26 |
| 85 | 16 | 26 |
| 90 | 16 | 26 |
| 95 | 16 | 26 |
| 100 | 16 | 26 |
| 110 | 16 | 21 |
| 120 | 15 | 21 |
| 130 | 15 | 21 |
| 140 | 15 | 21 |
| 150 | 15 | 21 |
| 160 | 15 | 21 |
| 170 | 15 | 21 |
| 180 | 15 | 21 |
| 190 | 15 | 21 |
| 200 | 15 | 21 |

Fractions 12–80 are combined, concentrated to an aqueous solution and freeze-dried to give prep ADA-34.1, 12.22 g.

In another series of experiments, 6 liters of fermentation broth containing 2 g of "inactivated" U-57930 is treated as described above. The methanolic eluates from the Amberlite XAD-2 column are kept as ADA-143B. This solution is not concentrated to dryness; instead, it is purified by Dowex-1 Chromatography as described below.

Dowex-1 Chromatography: The column is prepared from 300 ml of Dowex-1 (X-4) in the acetate form. The methanolic solution, ADA-143B pH 8.2 is passed through the column. The spent is collected at a rate of 2.5 ml/minute in 20 ml-fractions. (Fractions 1–60). The column is washed with 1.5 liter of water (10 ml/min; fractions 66–108). The column is then eluted with 5% acetic acid (rate, 10 ml/minute; fractions 109–310). The following pools are made:

| Pool 1 | Fractions 1–80 | 1000 ml | (ADA-1A) |
| --- | --- | --- | --- |
| 2 | Fractions 81–110 | 600 ml | (ADA-2A) |
| 3 | Fractions 111–130 | 450 ml | (ADA-3A) |
| 4 | Fractions 131–150 | 450 ml | (ADA-4A) |
| 5 | Fractions 151–190 | 900 ml | (ADA-5A) |
| 6 | Fractions 191–230 | 900 ml | (ADA-6A) |
| 7 | Fractions 231–270 | 900 ml | (ADA-7A) |
| 8 | Fractions 271–310 | 900 ml | (ADA-8A) |

Testing before (−E) and after (+E) treatment with alkaline phosphatase shows the following:

| | Zone (*S. lutea*) | |
| --- | --- | --- |
| | −E | +E |
| Pool 1 | 31 | 52 |
| 2 | 36 | 49 |
| 3 | 34 | 45 |
| 4 | 18 | 40 |
| 5 | 25 | 30 |
| 6 | 27 | 29 |
| 7 | 27 | 29 |
| 8 | 29 | 31 |

Pools 1 and 2 are combined, concentrated to an aqueous solution and freeze-dried to give prep ADA-2.1, 1.48 g.

Pools 3 and 4 are also combined and treated similarly to give ADA-2.2, 2.5 g.

Preparations ADA-2.1 and -2.2 give U-57930 after treatment with alkaline phosphatase.

Preparations ADA-34.1, -2.1 and −2.2 are combined and purified by the counter double current distribution procedure described below.

Counter Double Current Distribution: The material obtained by combination of preparations ADA-34.1, -2.1 and -2.2, 16.20 g, is dissolved in 25 ml of each phase of the solvent system consisting of equal volumes of 1-butanol-water (1:1). The solutions are added in the center tubes of an all-glass counter double current distribution apparatus (100 tubes, 25 ml/phase). The distribution is analyzed, after 150 transfers, for bioactivity before (−E) and after (+E) treatment with alkaline phosphatase. Results follow:

|  | Zone (*S. lutea*-sensitive) | |
| --- | --- | --- |
|  | −E | +E |
| Lower Collector | | |
| 5 | 29 | 31 |
| 10 | 31 | 33 |
| 15 | 30 | 33 |
| 20 | 27 | 33 |
| 25 | 22 | 33 |
| 30 | 17 | 34 |
| 35 | 0 | 34 |
| 40 | 0 | 33.5 |
| 45 | 0 | 33 |
| 50 | 0 | 34 |
| 55 | 0 | 34 |
| 60 | 0 | 35 |
| 65 | 0 | 36 |
| 70 | 0 | 38 |
| 75 | 0 | 39 |
| 80 | 0 | 40 |
| 85 | 0 | 41 |
| 90 | 0 | 42 |
| 95 | 0 | 43 |
| 100 | 0 | 43.5 |
| Lower Machine | | |
| 50 | 0 | 45 |
| 45 | trace | 46 |
| 40 | 15 | 47 |
| 35 | 17 | 47.5 |
| 30 | 17 | 47 |
| 25 | 18 | 47 |
| 20 | 17.5 | 48 |
| 15 | 17 | 48 |
| 10 | 16 | 48 |
| 5 | 15 | 50 |
| 0 | trace | 50 |
| Upper Machine | | |
| 5 | trace | 49 |
| 10 | trace | 48.5 |
| 15 | trace | 48 |
| 20 | trace | 48.5 |
| 25 | trace | 49 |
| 30 | 30 | 50 |
| 35 | trace | 51 |
| 40 | 15 | 52 |
| 45 | 16 | 53 |
| 50 | 21 | 54 |
| Upper Collector | | |
| 100 | 17.5 | 54 |
| 95 | 17 | 53.5 |
| 90 | 19 | 53.5 |
| 85 | 20 | 53.5 |
| 80 | 21 | 53.5 |
| 75 | 22 | 53.5 |
| 70 | 24 | 53.5 |
| 65 | 26 | 53.5 |
| 60 | 28 | 53.5 |
| 55 | 30 | 52.5 |
| 50 | 32.5 | 52 |
| 45 | 33 | 52 |
| 40 | 35 | 52 |
| 35 | 36 | 52 |
| 30 | 39 | 49 |
| 25 | 41 | 47 |
| 20 | 43 | 48 |
| 15 | 43 | 46 |
| 10 | 43 | 43 |
| 5 | 35 | 35 |

The following pools are made. Each pool is concentrated to an aqueous solution and freeze-dried to give the corresponding preparations.
Pool I: Lower collector 1-50;
Pool II: Lower collector 51-100; lower machine 50-30;
Pool III: Lower machine 29-0; Upper machine 1-50; Upper collector 100-30.

Preparations obtained are:
From pool I, prep. ADA-47.1, 9.78 g
From pool II, prep. ADA-47.2, 0.30 g
From pool III, prep. ADA-47.3, 5.29 g Preparations ADA-47.2 and -47.3 are combined and purified by DEAE-Sephadex chromatography as described below.

DEAE-Sephadex Chromatography: Three hundred g of DEAE-Sephadex (A-25) are stirred for 1 hour with water and for 2 hours with 0.5 N aqueous sodium hydroxide. The ionic exchanger is washed with water until the pH is ca 7.5. The material is then stirred for 2 hours with 0.5 N aqueous acetic acid, washed with water to a neutral pH, and poured into a column and packed under 2 lbs pressure to a constant height. The column is washed with 4 liter of water, 8 liter of 0.1% aqueous solution of tris-(hydroxymethyl)aminomethane (THAM), and 3 liter of 0.03 M THAM acetate buffer pH 8.0 (prepared by dissolving 3.64 g of THAM in 800 ml water, adjusting the pH to 8.0 with glacial acetic acid and then adjusting the volume to 1 liter).

Starting material, preparations ADA-47.2 and 47.3 ca 5.50 g, is dissolved in 20 ml of 0.03 M THAM acetate pH 8.0 buffer and added on the top of the column. The column is then eluted downflow with 0.3 M THAM acetate pH 8.0 buffer. Fractions 1-190 (20 ml) are collected. At this point elution of the column is continued in an upflow manner. Fractions A, B, C, D, and E (1 liter each) are collected. Testing for bioactivity before (−E) and after (+E) treatment with alkaline phosphatase shows the following:

| Fraction No. | Zone (*S. lutea*-sensitive) | |
| --- | --- | --- |
|  | −E | +E |
| 3 | 0 | 0 |
| 6 | 0 | 0 |
| 9 | 0 | 0 |
| 12 | 0 | 0 |
| 15 | 0 | 0 |
| 18 | 0 | 0 |
| 21 | 0 | 0 |
| 24 | 0 | 0 |
| 27 | 0 | 0 |
| 30 | 0 | 0 |
| 33 | 0 | 0 |
| 36 | 38 | 39 |
| 39 | 43.5 | 44 |
| 42 | 36 | 36 |
| 45 | 23.5 | 23 |
| 48 | 15 | 16 |
| 51 | 0 | 0 |
| 54 | 0 | 0 |
| 57 | 0 | 0 |
| 60 | 0 | 0 |

-continued

| Fraction No. | Zone (*S. lutea*-sensitive) | |
|---|---|---|
| | −E | +E |
| 63 | 0 | 0 |
| 66 | 0 | 0 |
| 69 | 15 | 16 |
| 72 | 17 | 20 |
| 75 | 21 | 26 |
| 78 | 23 | 27 |
| 81 | 23 | 30 |
| 84 | 23 | 29 |
| 87 | 22 | 24 |
| 90 | 21 | 23 |
| 93 | 21 | 24 |
| 96 | 22 | 26 |
| 99 | 21 | 35 |
| 102 | 22 | 44 |
| 105 | 23 | 51 |
| 108 | 22.5 | 54 |
| 111 | 22.5 | 52.5 |
| 114 | 22 | 52 |
| 117 | 22 | 54.5 |
| 120 | 20.5 | 56 |
| 123 | 20 | 56 |

The following pools are made:

| Pool I | Fractions 34–38, | 280 ml | (ADA-69B) |
|---|---|---|---|
| Pool II | Fractions 75–90, | 330 ml | (ADA-69C) |
| Pool III | Fractions 101–111, | 180 ml | (ADA-69D) |
| Pool IV | Fractions 114–150, | 580 ml | (ADA-69E) |
| Pool V | Fractions 151–164, | 100 ml | (ADA-69F) |
| Pool VI | Fractions 165–186, | 125 ml | (ADA-69G) |
| Pool VII | Fraction C, | 1 liter | (ADA-69A) |

Pool I (ADA-69B) contains unchanged U-57930 and is discarded.

Pool II (ADA-69C) contains an unknown material which yields U-57930 by treatment with alkaline phosphatase. UV: λ max 275 nm.

Pool III (ADA-69D) contains U-57930 cytidylate and is treated as described later. UV λ max 270 nm.

Pool IV (ADA-69E) contains U-57930 adenylate and is treated as described later. UV: λ max 260 nm.

Pool V (ADA-69F) contains a mixture of U-57930 adenylate, U-57930 uridylate and U-57930 guanylate. This solution is treated as described later.

Pool VI (ADA-69G) contains U-57930 guanylate and is treated as described later. UV: λ max 254; sh at 275.

Pool VII (ADA-69A) contains a mixture of U-57930 guanylate and U-57930 uridylate. This solution is treated as described later.

Isolation of essentially Pure U-57930-Cytidylate, U-57930-Adenylate and U-57930-Guanylate from Pools III, IV and VI, Respectively. Removal of THAM Acetate Buffer by Amberlite XAD-2 Chromatography: Pools III, IV and VI, obtained as described above, are passed over columns containing Amberlite XAD-2. The spents are discarded. The columns are washed with water and then eluted with methanol-water (70:30 v/v). Fractions are analyzed by UV and by testing for bioactivity before and after treatment with alkaline phosphatase. Appropriate fractions are combined, concentrated to an aqueous solution and freeze-dried. Details on the amount of Amberlite XAD-2 used for each pool, the amount of water wash, the amount of methanolic eluate and the amount of material obtained are listed in the following table.

| Pool | Amberlite XAD-2 Used (ml) | Water Wash (ml) | Methanolic Eluate (ml) | Isolated Material (mg) |
|---|---|---|---|---|
| III | 50 | 200 | 300 | 150 |
| IV | 200 | 800 | 600 | 3510 |
| VI | 50 | 200 | 300 | 470 |

The material obtained from pool III is kept as ADA-73.1; from pool IV as ADA-74.1; and from pool VI as ADA-75.1.

Removal of THAM Acetate Buffer from Pool V (ADA-69F) and Pool VII (ADA-69A) by Amberlite XAD-2 Chromatography: The column is prepared from 300 ml of Amberlite XAD-2. Pools V and VII containing a mixture of U-57930 adenylate; U-57930-uridylate and U-57930 guanylate are passed through the column. The spent is discarded. The column is washed with 600 ml of water. The spent is discarded. The column is eluted with methanol-water (70:30). Fractions yielding bioactive material after treatment with alkaline phosphatase are combined, 300 ml, concentrated to an aqueous solution and freeze-dried to give prep ADA-71.1, 670 mg. Prep -71.1 is treated as described below.

Separation of U-57930 Uridylate from U-57930-Adenylate and U-57930-Guanylate. DEAE-Sephadex Chromatography. Six hundred ml of DEAE-Sephadex in the acetate form, prepared as described earlier, are washed with 0.03 M THAM acetate pH 8.0 buffer and packed into a glass column (ID, 4.5 cm; height, 40 cm) under hydrostatic pressure.

Prep ADA-71.1 (see above) is dissolved in 10 ml of 0.03 M THAM acetate pH 8.0 buffer and added on the top of the column. The column is eluted with:
(1) 0.03 M THAM acetate, pH 8.0 (Fractions 1-79)
(2) 0.12 M THAM acetate, pH 8.0 (Fractions 80-395)
(3) 0.25 M THAM acetate, pH 8.0 (Fractions 396-750)

Fractions of 20 ml are collected and analyzed by UV and by testing for bioactivity before and after treatment with alkaline phosphatase. Fractions 51-60 contain U-57930 adenylate; fractions 62-73 (ADA-94.B) contain U-57930 uridylate; fractions 75-110 contain U-57930 guanylate).

Isolation of Essentially Pure U-57930 Uridylate. Removal of THAM-Acetate Buffer by Amberlite XAD-2 Chromatography. The column is prepared from 50 ml of Amberlite XAD-2. Pool ADA-94B, containing U-57930 uridylate, is passed over the column at a rate of 2 ml/minute. The spent is discarded. The column is washed with 200 ml of water. The wash is discarded. The column is eluted with methanol-water (70:30 v/v). Fractions containing (by UV) U-57930 uridylate are combined (200 ml), concentrated to an aqueous solution, and freeze-dried to give ADA-95.1, 60 mg.

CHARACTERIZATION OF U-57930 3'(5'-CYTIDYLATE)

1. IR Tabulation

Tables listing the IR absorptions (Nujol and KBr) are as follows:

| Band Freq. | Inten. | Type | Band Freq. | Inten. | Type |
|---|---|---|---|---|---|
| 3417.3 | 24 | SH | 1249.0 | 33 | SH |
| 3341.1 | 19 | BRD | 1214.3 | 21 | AVG |
| 3211.8 | 19 | BRD | 1146.8 | 42 | SH |
| 3108.6 | 25 | BRD | 1089.9 | 15 | BRD |

-continued

| Band Freq. | Inten. | Type | Band Freq. | Inten. | Type |
|---|---|---|---|---|---|
| 2951.4 | 2 | BRD M | 1070.6 | 12 | AVG |
| 2926.3 | 1 | BRD M | 1056.1 | 14 | SH |
| 2854.9 | 2 | BRD M | 992.4 | 39 | AVG |
| 2729.6 | 48 | BRD M | 972.2 | 39 | AVG |
| 2693.9 | 51 | SH | 955.8 | 49 | SH |
| 2535.7 | 65 | SH | 930.7 | 51 | AVG |
| 1649.3 | 8 | AVG | 889.2 | 36 | AVG |
| 1610.7 | 26 | AVG | 860.3 | 52 | AVG |
| 1575.0 | 35 | AVG | 849.7 | 53 | AVG |
| 1528.7 | 31 | AVG | 804.4 | 46 | SH |
| 1489.2 | 23 | AVG | 788.9 | 40 | AVG |
| 1462.2 | 9 | AVG M | 721.4 | 44 | AVG M |
| 1404.3 | 41 | BRD | 705.0 | 47 | BRD |
| 1377.3 | 18 | AVG M | 654.9 | 45 | SH |
| 1368.6 | 31 | SH M | 632.7 | 38 | AVG |
| 1286.6 | 34 | AVG | | | |

Band Freq.: Band Frequencies in Wavenumbers (cm-1)
Inten.: Intensity in percent transmittance (% T)
Data Type in Local Peak Region: BRD—Broad; AVG—Average; SHP—Sharp; SH—Shoulder
Peak list edited.
*Indicates peaks added.
M: Possible interference from mineral oil.

| 25 Strongest Peaks | | | |
|---|---|---|---|
| % T | Freq. | % T | Freq. |
| 1 | 2926.2 | 24 | 3417.2 |
| 2 | 2951.3 | 25 | 3108.5 |
| 2 | 2854.8 | 26 | 1610.6 |
| 8 | 1649.2 | 31 | 1528.6 |
| 9 | 1462.1 | 31 | 1368.5 |
| 12 | 1070.5 | 33 | 1249.0 |
| 14 | 1056.0 | 34 | 1286.5 |
| 15 | 1089.8 | 35 | 1575.0 |
| 18 | 1377.2 | 36 | 889.1 |
| 19 | 3341.0 | 38 | 632.6 |
| 19 | 3211.7 | 39 | 992.3 |
| 21 | 1214.2 | 39 | 972.1 |
| 23 | 1489.1 | | |

Prep: Mineral Oil Mull
Max % T: 87 @ 1848.0
% T at 3800 (cm-1): 83
Density (cm-1/pt): 0.964

| Band Freq. | Inten. | Type | Band Freq. | Inten. | Type |
|---|---|---|---|---|---|
| 3408.6 | 10 | BRD | 1088.9 | 12 | BRD |
| 3102.8 | 26 | SH | 1071.5 | 9 | AVG |
| 2963.9 | 28 | AVG | 1057.1 | 11 | SH |
| 2930.2 | 27 | BRD | 992.4 | 35 | AVG |
| 2878.1 | 37 | AVG | 972.2 | 36 | AVG |
| 2862.7 | 39 | SH | 956.8 | 45 | SH |
| 2768.1 | 51 | SH | 928.8 | 48 | AVG |
| 2511.6 | 65 | BRD | 889.2 | 32 | AVG |
| 1649.3 | 4 | AVG | 859.3 | 47 | AVG |
| 1614.6 | 20 | SH | 851.6 | 47 | SH |
| 1576.0 | 30 | AVG | 804.4 | 39 | SH |
| 1528.7 | 28 | AVG | 788.9 | 34 | SH |
| 1491.1 | 21 | AVG | 743.6 | 47 | SH |
| 1462.2 | 33 | AVG | 705.0 | 40 | AVG |
| 1450.6 | 35 | SH | 654.9 | 39 | SH |
| 1404.3 | 37 | AVG | 634.6 | 35 | AVG |
| 1384.0 | 33 | AVG | 595.1 | 33 | AVG |
| 1360.9 | 42 | SH | 572.9 | 33 | AVG |
| 1286.6 | 32 | AVG | 525.6 | 32 | AVG |
| 1251.9 | 30 | SH | 447.5 | 36 | AVG |
| 1215.2 | 18 | AVG | | | |

Band Freq.: Band Frequencies in wavenumbers (cm-1)
Inten.: Intensity in Percent Transmittance (% T)
Data Type in Local Peak Region: BRD—Broad; AVG—Average; SHP—Sharp; SH—Shoulder
Peak List Edited.
*Indicates peaks added.

| 25 Strongest Peaks | | | |
|---|---|---|---|
| % T | Freq. | % T | Freq. |
| 4 | 1649.2 | 30 | 1251.8 |
| 9 | 1071.5 | 32 | 1286.5 |
| 10 | 3408.5 | 32 | 889.1 |
| 11 | 1057.0 | 32 | 525.5 |
| 12 | 1088.8 | 33 | 1462.1 |
| 18 | 1215.1 | 33 | 1384.0 |
| 20 | 1614.5 | 33 | 595.0 |
| 21 | 1491.0 | 33 | 572.8 |
| 26 | 3102.7 | 34 | 788.8 |
| 27 | 2930.1 | 35 | 1450.5 |
| 28 | 2963.8 | 35 | 992.3 |
| 28 | 1528.6 | 35 | 634.5 |
| 30 | 1576.0 | | |

Prep: KBR Pellet
Max % T: 100 @ 403.1
% T at 4000 (cm-1): 78
Density (cm-1/pt): 0.964

2. UV Absorption Spectrum [λmax (a)]
In water at:
pH 2.0, 279 nm (6.5)
pH 7.0, 270 nm (9.9)
pH 11.0, 271 (9.6)

3. Elemental Composition
Mol. formula: $C_{26}H_{43}N_5O_{12}$ SClP. Molecular Weight, 715. Calcd: C, 43.64; H, 6.01; N, 9.79; O, 26.88; S, 4.47; Cl, 4.89; P, 4.33.

4. Optical Rotation
$[\alpha]_D^{25}$, +107° (C, 0.854, water)

5. Solubilities
Highly soluble in water, methanol and ethanol. Slightly soluble in acetone and other ketones, ethyl acetate and other esters, chloroform, methylene chloride. Insoluble in saturated hydrocarbon solvents.

6. Antibacterial Activity
U-57930 3-(5'-cytidylate) is not active in vitro. However, treatment with alkaline phosphatase or phosphodiesterase I yields U-57930 which is highly active against a variety of G+ organisms, both in vitro and in vivo.

7. Melting point: 205°–207° (with decomposition).

CHARACTERIZATION OF U-57930 3'(5'-ADENYLATE)

1. IR Tabulation
Tables listing the IR absorptions (Nujol and KBr) are as follows:

| Band Freq. | Inten. | Type | Band Freq. | Inten. | Type |
|---|---|---|---|---|---|
| 3335.3 | 16 | BRD | 1245.1 | 24 | SH |
| 3267.8 | 17 | BRD | 1213.3 | 17 | AVG |
| 3210.8 | 17 | BRD | 1175.7 | 43 | SH |
| 2954.3 | 3 | BRD M | 1146.8 | 40 | SH |
| 2924.4 | 2 | BRD M | 1089.9 | 13 | AVG |
| 2868.4 | 6 | SH M | 1069.6 | 10 | AVG |
| 2854.9 | 4 | AVG M | 1055.1 | 13 | SH |
| 2727.6 | 46 | BRD M | 991.5 | 35 | AVG |
| 2520.2 | 61 | BRD | 972.2 | 36 | AVG |
| 1684.0 | 22 | SH | 957.7 | 45 | AVG |
| 1641.6 | 14 | AVG | 930.7 | 48 | AVG |
| 1600.1 | 28 | AVG | 889.2 | 32 | AVG |
| 1576.0 | 31 | AVG | 861.3 | 47 | AVG |
| 1550.9 | 43 | SH | 848.7 | 49 | AVG |
| 1509.4 | 53 | SH | 818.8 | 45 | AVG |
| 1463.1 | 15 | AVG M | 798.6 | 40 | AVG |
| 1420.7 | 35 | AVG | 722.4 | 36 | AVG M |
| 1377.3 | 24 | AVG M | 708.9 | 40 | SH |
| 1367.6 | 35 | SH M | 647.1 | 33 | SH |
| 1332.0 | 36 | AVG | 635.6 | 31 | AVG |

-continued

| Band Freq. | Inten. | Type | Band Freq. | Inten. | Type |
|---|---|---|---|---|---|
| 1299.2 | 34 | AVG | | | |

Band Freq.: Band Frequencies in Wavenumbers (cm-1)
Inten.: Intensity in percent transmittance (% T)
Data Type in Local Peak Region: BRD—Broad; AVG—Average; SHP—Sharp; SH—Shoulder
Peak list edited.
*Indicates peaks added.
M: Possible interference from mineral oil.

25 Strongest Peaks

| % T | Freq. | % T | Freq. |
|---|---|---|---|
| 2 | 2924.3 | 22 | 1684.0 |
| 3 | 2954.2 | 24 | 1377.2 |
| 4 | 2854.8 | 24 | 1245.0 |
| 6 | 2868.3 | 28 | 1600.0 |
| 10 | 1069.5 | 31 | 1576.0 |
| 13 | 1089.8 | 31 | 635.5 |
| 13 | 1055.0 | 32 | 889.1 |
| 14 | 1641.5 | 33 | 647.0 |
| 15 | 1463.0 | 34 | 1299.1 |
| 16 | 3335.2 | 35 | 1420.6 |
| 17 | 3267.7 | 35 | 1367.5 |
| 17 | 3210.7 | 35 | 991.5 |
| 17 | 1213.2 | | |

Prep: Mineral Oil Mull
Max % T: 85 @ 1864.4
% T at 3800 (cm-1): 81
Density (cm-1/pt): 0.964

| Band Freq. | Inten. | Type | Band Freq. | Inten. | Type |
|---|---|---|---|---|---|
| 3375.8 | 7 | BRD | 1090.8 | 8 | AVG |
| 3223.4 | 10 | BRD | 1069.6 | 5 | AVG |
| 3124.0 | 17 | SH | 1050.3 | 8 | SH |
| 2963.0 | 22 | AVG | 990.5 | 27 | AVG |
| 2929.2 | 22 | BRD | 972.2 | 29 | AVG |
| 2878.1 | 31 | AVG | 956.8 | 38 | SH |
| 2863.6 | 33 | SH | 929.8 | 42 | AVG |
| 2756.6 | 45 | BRD | 889.2 | 24 | AVG |
| 2521.2 | 60 | BRD | 861.3 | 38 | AVG |
| 2188.5 | 75 | BRD | 851.6 | 40 | SH |
| 1678.2 | 15 | SH | 818.8 | 36 | AVG |
| 1643.5 | 7 | AVG | 807.3 | 36 | BRD |
| 1602.0 | 20 | AVG | 798.6 | 30 | AVG |
| 1576.0 | 23 | AVG | 768.7 | 41 | BRD |
| 1553.8 | 35 | SH | 721.4 | 30 | AVG |
| 1511.4 | 49 | SH | 706.9 | 31 | BRD |
| 1475.7 | 27 | AVG | 648.1 | 26 | AVG |
| 1421.7 | 29 | AVG | 636.5 | 26 | AVG |
| 1384.0 | 32 | AVG | 584.5 | 28 | SH |
| 1332.0 | 31 | AVG | 571.9 | 26 | AVG |
| 1301.1 | 28 | AVG | 533.3 | 27 | SH |
| 1246.1 | 19 | SH | 522.7 | 25 | AVG |
| 1215.2 | 12 | AVG | 503.4 | 25 | AVG |
| 1176.7 | 36 | SH | | | |

Band Freq.: Band Frequencies in Wavenumbers (cm-1)
Inten.: Intensity in percent transmittance (% T)
Data Type in Local Peak Region: BRD—Broad; AVG—Average; SHP—Sharp; SH—Shoulder
Peak list edited.
*Indicates peaks added.

25 Strongest Peaks

| % T | Freq. | % T | Freq. |
|---|---|---|---|
| 5 | 1069.5 | 23 | 1576.0 |
| 7 | 3375.7 | 24 | 889.1 |
| 7 | 1643.5 | 25 | 522.6 |
| 8 | 1090.7 | 25 | 503.3 |
| 8 | 1050.2 | 26 | 648.0 |
| 10 | 3223.3 | 26 | 636.5 |
| 12 | 1215.1 | 26 | 571.8 |
| 15 | 1678.1 | 27 | 1475.6 |
| 17 | 3124.0 | 27 | 990.5 |
| 19 | 1246.0 | 27 | 533.2 |
| 20 | 1602.0 | 28 | 1301.0 |
| 22 | 2963.0 | 28 | 584.5 |
| 22 | 2929.1 | | |

Prep: KBR Pellet
Max % T: 95 @ 405.0
% T at 4000 (cm-1): 77
Density (cm-1/pt): 0.964

2. UV Absorption Spectrum [λmax (a)]
In water at:
pH 2.0, 258 (16.0)
pH 7.0, 261 (16.5)
pH 11.0, 261 (16.0)

3. Elemental Composition
Molecular formula: $C_{27}H_{43}N_7O_{10}$ SClP. Molecular Weight, 723. Calcd C, 44.81; H, 5.94; N, 13.55; O, 22.13; S, 4.42; Cl, 4.84; P, 4.28. Found N, 12.87; S, 5.39; Cl, 4.76; P, 3.83.

4. Optical Rotation
$[\alpha]_D^{25}$, +94° (C, 0.887, water).

5. Solubilities
Highly soluble in water, methanol and ethanol. Slightly soluble in acetone and other ketones, ethyl acetate and other esters, chloroform and methylene chloride. Insoluble in saturated hydrocarbon solvents.

6. Antibacterial Activity
U-57930 [3-(5'-adenylate)] is not active in vitro. However, treatment with alkaline phosphatase or phosphodiester I yields U-57930, which is highly active against a variety of G+ organisms both in vitro and in vivo. U-57930 3-(5'-adenylate) was found active in vivo (subcutaneously, mice) with a $CD_{50}$ of 0.62 (0.48–0.79) mg/kg. against S. pyogenes.

7. Melting Point: 203.5°–205° (with decomposition)

CHARACTERIZATION OF U-57930 3-(5'-URIDYLATE)

1. IR Tabulation
Tables listing the IR absorptions (Nujol and KBr) are as follows:

| Band Freq. | Inten. | Type | Band Freq. | Inten. | Type |
|---|---|---|---|---|---|
| 3330.4 | 19 | BRD | 1332.9 | 44 | BRD |
| 3224.4 | 21 | BRD | 1296.3 | 40 | SH |
| 2952.4 | 1 | BRD M | 1251.9 | 28 | BRD |
| 2924.4 | 0 | BRD M | 1215.2 | 19 | AVG |
| 2867.5 | 4 | SH M | 1089.9 | 13 | AVG |
| 2854.0 | 3 | AVG M | 1071.5 | 9 | AVG |
| 2733.4 | 49 | SH M | 1056.1 | 13 | SH |
| 2695.8 | 53 | SH | 991.5 | 39 | AVG |
| 2532.8 | 67 | SH | 973.2 | 39 | AVG |
| 1757.3 | 73 | SH | 957.7 | 48 | SH |
| 1685.9 | 8 | AVG | 931.7 | 49 | AVG |
| 1647.4 | 21 | SH | 890.2 | 34 | AVG |
| 1602.0 | 41 | AVG | 858.4 | 50 | AVG |
| 1574.1 | 42 | AVG | 813.0 | 43 | AVG |
| 1555.7 | 43 | BRD | 798.6 | 47 | AVG |
| 1462.2 | 12 | AVG M | 767.7 | 50 | AVG |
| 1425.5 | 37 | SH | 721.4 | 42 | AVG M |
| 1378.3 | 22 | AVG M | 634.6 | 35 | AVG |

-continued

| Band Freq. | Inten. | Type | Band Freq. | Inten. | Type |
|---|---|---|---|---|---|
| 1367.6 | 37 | SH M | | | |

Band Freq.: Band Frequencies in Wavenumbers (cm-1)
Inten.: Intensity in percent transmittance (% T)
Data Type in Local Peak Region: BRD—Broad; AVG—Average; SHP—Sharp; SH—Shoulder
This peak list is unedited.
M: Possible interference from mineral oil.

| 25 Strongest Peaks | | | |
|---|---|---|---|
| % T | Freq. | % T | Freq. |
| 0 | 2924.3 | 22 | 1378.2 |
| 1 | 2952.3 | 28 | 1251.8 |
| 3 | 2854.0 | 34 | 890.1 |
| 4 | 2867.5 | 35 | 634.5 |
| 8 | 1685.8 | 37 | 1425.5 |
| 9 | 1071.5 | 37 | 1367.5 |
| 12 | 1462.1 | 39 | 991.5 |
| 13 | 1089.8 | 39 | 973.1 |
| 13 | 1056.0 | 40 | 1296.2 |
| 19 | 3330.3 | 41 | 1602.0 |
| 19 | 1215.1 | 42 | 1574.0 |
| 21 | 3224.3 | 42 | 721.3 |
| 21 | 1647.3 | | |

Prep: Mineral Oil Mull
Max % T: 86 @ 3764.5
% T at 3800 (cm-1): 85
Density (cm-1/pt): 0.964

| Band Freq. | Inten. | Type | Band Freq. | Inten. | Type |
|---|---|---|---|---|---|
| 3387.4 | 12 | BRD | 1055.1 | 10 | SH |
| 3114.4 | 25 | SH | 992.4 | 35 | AVG |
| 2962.0 | 26 | AVG | 973.2 | 36 | AVG |
| 2931.1 | 26 | BRD | 956.8 | 45 | SH |
| 2879.1 | 36 | AVG | 929.8 | 48 | AVG |
| 2863.6 | 38 | SH | 889.2 | 31 | AVG |
| 2833.7 | 43 | SH | 859.3 | 46 | AVG |
| 2509.6 | 64 | BRD | 813.0 | 40 | AVG |
| 1685.0 | 6 | BRD | 811.1 | 40 | SH |
| 1647.4 | 17 | SH | 798.6 | 43 | AVG |
| 1605.9 | 35 | SH | 782.2 | 48 | BRD |
| 1576.0 | 37 | AVG | 768.7 | 48 | AVG |
| 1556.7 | 39 | BRD | 707.9 | 43 | AVG |
| 1463.1 | 31 | AVG | 669.3 | 43 | SH |
| 1423.6 | 35 | AVG | 649.1 | 40 | SH |
| 1384.0 | 32 | AVG | 634.6 | 37 | AVG |
| 1331.0 | 43 | AVG | 585.4 | 38 | SH |
| 1297.2 | 38 | SH | 567.1 | 34 | AVG |
| 1255.8 | 24 | AVG | 523.7 | 35 | AVG |
| 1214.3 | 17 | AVG | 447.5 | 39 | AVG |
| 1090.8 | 10 | AVG | | | |
| 1070.6 | 7 | AVG | | | |

Band Freq.: Band Frequencies in Wavenumbers (cm-1)
Inten.: Intensity in percent transmittance (% T)
Data Type in Local Peak Region: BRD—Broad; AVG—Average; SHP—Sharp; SH—Shoulder
Peak List Edited.
*Indicates peaks added.

| 25 Strongest Peaks | | | |
|---|---|---|---|
| % T | Freq. | % T | Freq. |
| 6 | 1685.0 | 32 | 1384.0 |
| 7 | 1070.5 | 34 | 567.0 |
| 10 | 1090.7 | 35 | 1605.8 |
| 10 | 1055.0 | 35 | 1423.5 |
| 12 | 3387.3 | 35 | 992.3 |
| 17 | 1647.3 | 35 | 523.6 |
| 17 | 1214.2 | 36 | 2879.0 |
| 24 | 1255.7 | 36 | 973.1 |
| 25 | 3114.3 | 37 | 1576.0 |
| 26 | 2962.0 | 37 | 634.5 |

| 25 Strongest Peaks | | | |
|---|---|---|---|
| % T | Freq. | % T | Freq. |
| 26 | 2931.0 | 38 | 2863.5 |
| 31 | 1463.0 | 38 | 1297.1 |
| 31 | 889.1 | | |

Prep: KBR Pellet
Max % T: 101 @ 405.0
% T at 4000 (cm-1): 76
Density (cm-1/pt): 0.964

2. UV Absorption Spectrum [λmax (a)]
In water at:
pH 2.0, 261 (11.5)
pH 7.0, 262 (10.7)
pH 11.0, 262 (11.5)

3. Elemental Composition
Molecular formula: $C_{26}H_{42}N_4O_{13}$ SClP. Molecular Weight, 716. Calcd C, 43.57; H, 5.86; N, 7.82; O, 29.05; S, 4.46; Cl, 4.89; P, 4.33.

4. Optical Rotation
$[\alpha]_D^{25} + 105°$ (C, 0.94, water)

5. Solubilities
Highly soluble in water, methanol and ethanol. Slightly soluble in acetone and other ketones, ethyl acetate and other esters, chloroform and methylene chloride. Insoluble in saturated hydrocarbon solvents.

6. Antibacterial Activity
U-57930 3-(5'-uridylate) is not active in vitro. However, treatment with alkaline phosphatase or phosphodiesterase I yields U-57930 which is highly active against a variety of G+ organisms both in vitro and in vivo.

7. Melting Point: 202°–203° (with decomposition)

CHARACTERIZATION OF U-57930 3-(5'-GUANYLATE)

1. Tables listing the IR absorptions (Nujol and KBr) are as follows:

| Band Freq. | Inten. | Type | Band Freq. | Inten. | Type |
|---|---|---|---|---|---|
| 3335.3 | 16 | BRD | 1250.0 | 36 | SH |
| 3227.2 | 19 | BRD | 1213.3 | 21 | AVG |
| 2953.3 | 2 | AVG M | 1173.8 | 39 | AVG |
| 2925.3 | 1 | BRD M | 1149.7 | 41 | AVG |
| 2868.4 | 6 | SH M | 1087.9 | 14 | SH |
| 2855.9 | 4 | AVG M | 1071.5 | 9 | AVG |
| 2737.3 | 51 | BRD M | 991.5 | 42 | AVG |
| 2521.2 | 73 | BRD | 972.2 | 42 | AVG |
| 1684.0 | 6 | AVG | 956.8 | 52 | SH |
| 1635.8 | 11 | AVG | 929.8 | 51 | AVG |
| 1598.2 | 21 | AVG | 890.2 | 36 | AVG |
| 1572.1 | 26 | AVG | 860.3 | 51 | AVG |
| 1534.5 | 34 | AVG | 800.5 | 46 | AVG |
| 1462.2 | 18 | AVG M | 783.1 | 42 | SHP |
| 1414.9 | 44 | AVG | 720.4 | 43 | AVG M |
| 1377.3 | 24 | AVG M | 707.9 | 45 | BRD |
| 1365.7 | 31 | AVG | 681.9 | 40 | AVG |
| 1312.7 | 44 | AVG | 635.6 | 34 | AVG |

Band Freq.: Band Frequencies in Wavenumbers (cm-1)
Inten.: Intensity in Percent Transmittance (% T)
Data Type in Local Peak Region: BRD—Broad; AVG—Average; SHP—Sharp; SH—Shoulder
Peak List Edited.
*Indicates Peaks Added.
M: Possible interference from Mineral Oil

| 25 Strongest Peaks | | | |
|---|---|---|---|
| % T | Freq. | % T | Freq. |
| 1 | 2925.2 | 24 | 1377.2 |

-continued

| 25 Strongest Peaks | | | |
|---|---|---|---|
| % T | Freq. | % T | Freq. |
| 2 | 2953.2 | 26 | 1572.0 |
| 4 | 2855.8 | 31 | 1365.6 |
| 6 | 2868.3 | 34 | 1534.5 |
| 6 | 1684.0 | 34 | 635.5 |
| 9 | 1071.5 | 36 | 1250.0 |
| 11 | 1635.7 | 36 | 890.1 |
| 14 | 1087.8 | 39 | 1173.7 |
| 16 | 3335.2 | 40 | 681.8 |
| 18 | 1462.1 | 41 | 1149.6 |
| 19 | 3227.1 | 42 | 991.5 |
| 21 | 1598.1 | 42 | 972.1 |
| 21 | 1213.2 | | |

Prep: Mineral Oil Mull
Max % T: 97 @ 3762.6
% T at 3800 (cm-1): 97
Density (cm-1/pt): 0.964

| Band Freq. | Inten. | Type | Band Freq. | Inten. | Type |
|---|---|---|---|---|---|
| 3380.6 | 9 | BRD | 1174.7 | 31 | AVG |
| 3234.0 | 13 | BRD | 1147.7 | 33 | BRD |
| 2963.0 | 22 | AVG | 1088.9 | 9 | BRD |
| 2929.2 | 21 | BRD | 1070.6 | 6 | AVG |
| 2878.1 | 31 | AVG | 991.5 | 33 | AVG |
| 2862.7 | 33 | SH | 972.2 | 34 | AVG |
| 2744.0 | 44 | BRD | 956.8 | 43 | SH |
| 2522.2 | 61 | BRD | 929.8 | 44 | AVG |
| 1683.0 | 4 | BRD | 889.2 | 28 | AVG |
| 1634.8 | 6 | AVG | 860.3 | 41 | AVG |
| 1598.2 | 14 | AVG | 800.5 | 36 | AVG |
| 1571.2 | 19 | AVG | 783.1 | 32 | AVG |
| 1534.5 | 26 | AVG | 715.6 | 38 | SH |
| 1482.4 | 38 | AVG | 705.0 | 38 | SH |
| 1461.2 | 36 | AVG | 679.9 | 33 | AVG |
| 1448.7 | 36 | BRD | 635.6 | 31 | AVG |
| 1413.9 | 34 | AVG | 584.5 | 34 | SH |
| 1384.0 | 29 | AVG | 571.9 | 32 | AVG |
| 1359.9 | 30 | AVG | 523.7 | 31 | AVG |
| 1312.7 | 37 | AVG | 502.5 | 30 | AVG |
| 1250.9 | 29 | SH | 447.5 | 34 | AVG |
| 1213.3 | 16 | AVG | | | |

Band Freq.: Band Frequencies in Wavenumbers (cm-1)
Inten.: Intensity in Percent Transmittance (% T)
Data Type in Local Peak Region: BRD—Broad; AVG—Average; SHP—Sharp; SH—Shoulder
Peak List Edited.
*Indicates Peaks Added.

| 25 Strongest Peaks | | | |
|---|---|---|---|
| % T | Freq. | % T | Freq. |
| 4 | 1683.0 | 29 | 1384.0 |
| 6 | 1634.7 | 29 | 1250.8 |
| 6 | 1070.5 | 30 | 1359.8 |
| 9 | 3380.5 | 30 | 502.5 |
| 9 | 1088.8 | 31 | 2878.0 |
| 13 | 3234.0 | 31 | 1174.6 |
| 14 | 1598.1 | 31 | 635.5 |
| 16 | 1213.2 | 31 | 523.6 |
| 19 | 1571.1 | 32 | 783.0 |
| 21 | 2929.1 | 32 | 571.8 |
| 22 | 2963.0 | 33 | 2862.6 |
| 26 | 1534.5 | 33 | 1147.6 |
| 28 | 889.1 | | |

Prep: KBR Pellet
Max % T: 97 @ 405.0
% T at 400 (cm-1): 77
Density (cm:1/pt): 0.964

2. UV Absorption Spectrum [λmax (a)]
In water at:
pH 2.0, 256 (13.4); 280 (8.4) sh
pH 7.0, 254 (14.5); 273 (9.7) sh
pH 11.0, 259 (12.6); 266 (12.4) sh 3. Elemental Composition
Molecular formula: $C_{27}H_{43}N_7O_{11}$ SCIP. Molecular Weight 739. Calcd C, 43.84; H, 5.81; N, 13.26; O, 23.27; S, 4.33; Cl, 4.73; P, 4.19. Found N, 13.32; S, 4.86; Cl, 4.49; P, 3.25.

4. Optical Rotation
$[α]_D^{25}$, +97° (C, 0.855, water)

5. Solubilities
Highly soluble in water, methanol and ethanol. Slightly soluble in acetone and other ketones, ethyl acetate and other esters, chloroform and methylene chloride. Insoluble in saturated hydrocarbon solvents.

6. Antibacterial Activity
U-57930 3-(5'-guanylate) is not active in vitro. However, treatment with alkaline phosphatase or phosphodiesterase I yields U-57930 which is highly active against a variety of G+ organisms both in vitro and in vivo.

7. Melting Point: 219°–220° (with decomposition)

Since the compounds of the subject invention are active against various Gram-positive and Gram-negative microbes, they can be used in various environments to inhibit such microbes. For example, they can be used as disinfectants to inhibit S. aureus on washed and stacked food utensils contaminated with this bacterium. They also can be used as disinfectants on various dental and medical equipment contaminated with S. aureus. Further, the compounds of the invention can be used as bacteriostatic rinses for laundered clothes, and for impregnating papers and fabrics; and, they are also useful for suppressing the growth of sensitive organisms in plate assays and other microbiological media.

The compounds of the present invention are also useful in the treatment of diseases caused by members of the genus Mycoplasma, the most commonly known forms are PPLO (pleuropneumonia-like organisms) such as M. hominis, M. salivarium, M. mycoides, M. hyopneumonia, M. hyorhinis, M. gallisepticum, M. arthriditis and other species in man and animals, including domestic animals such as sheep, dogs, cattle, swine, and poultry (e.g., chickens, turkeys, ducks, and geese) and laboratory animals (e.g., rats and mice).

The U-57930 3-(5'-ribonucleotides) can be used in the treatment of kidney and other infections when L forms of gram-negative and gram-positive bacteria are present, for example, L forms of P. mirabilis.

Since the compounds of the subject invention are amphoteric substances, they can form salts with both acids and bases by using standard procedures. Examples of inorganic acids which can be used to form salts are hydrochloric, sulfuric, phosphoric, and the like. Examples of inorganic bases are sodium, potassium, calcium, lithium, and the like. Salts of the compounds can be used for the same purposes as the parent compounds.

The compounds of the subject invention are useful as antibacterial agents in suitable compositions. These compositions are preferably presented for administration to humans and animals in unit dosage forms, such as tablets, capsules, pills, powders, granules, sterile parenteral solutions or suspensions, and oral solutions or suspensions, and oil-water emulsions containing suitable quantities or the active compound in the form of the free base, or its pharmacologically acceptable salts.

For oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or othewise compounded to provide a dosage form affording the advantage of prolonged or delayed action or predetermined successive action of the enclosed medication. For example, the tablet can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixture of polymeric acids with such materials as shellac, cetyl alcohol, cellulose acetate phthalate, styrene maleic acid copolymer and the like. Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the compound of the formulation with an inert pharmaceutical diluent and filling the mixture into a hard gelatin capsule of appropriate size. In another embodiment, capsules are prepared by filling hard gelatin capsules with polymeric acid coated beads containing a compound of the formulas. Soft gelatin capsules are prepared by machine encapsulation of a slurry of a compound of the formulas with an acceptable vegetable oil, light liquid petrolatum or other inert oil.

Fluid unit dosage forms for oral administration such as syrups, elixirs, and suspensions can be prepared. The water-soluble forms of a compound of the formulas can be dissolved in an aqueous vehicle together with sugar, aromatic flavoring agents and preservatives to form a syrup. An elixir is prepared by using a hydroalcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose, and the like.

Topical ointments can be prepared by dispersing the active compound in a suitable ointment base such as petrolatum, lanolin, polyethylene glycols, mixtures thereof, and the like. Advantageously, the compound is finely divided by means of a colloid mill utilizing light liquid petrolatum as a levigating agent prior to dispersing in the ointment base. Topical creams and lotions are prepared by dispersing the compound in the oil phase prior to the emulsification of the oil phase in water.

For parenteral administration, fluid unit dosage forms are prepared utilizing a compound of the formulas and a sterile vehicle, water being preferred. The compound, depending on the form and concentrated used, can be either suspended or dissolved in the vehicle. In preparing solutions, a water-soluble form of a compound of the formulas can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. For sustained action, an intramuscular suspension is prepared with an insoluble form such as the trimethylsilyl ether or the pamoate salt. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfuls, tablespoonfuls, dropperfuls, ampuls, vials, segregated multiples of any of the foregoing, and other forms as herein described.

An active compound is compounded with a suitable pharmaceutical carrier in unit dosage form for convenient and effective administration. In the preferred embodiments of this invention, the dosage units contain 10, 25, 50, 100, 250, and 500 mg amounts of a compound of the formulas for systemic treatment; 5 to 65 percent w/v for parenteral treatment. The dosage of compositions containing an active compound and one or more other active ingredients is to be determined with reference to the usual dosage of each such ingredient.

The following examples are illustrative of the best mode contemplated by the inventor for carrying out his invention and are not to be construed as limiting.

The examples use the 3-(5'-ribonucleotide) of U-58,930E or U-60,970E as the active compound, but it should be understood that this is only exemplary of the other active compounds of the subject invention. U-60,970E is the 4-cis-n-butyl-L-pipecolic acid amide of 7-Cl-methylthiolincosaminide. Its preparation is shown in Example 7 of U.S. patent application Ser. No. 148,056.

Reference hereinafter to U-57,930E or U-60,970E means the 3-(5'-ribonucleotide) of these compounds. The 3-ribonucleotides are those as disclosed herein.

Composition Example 1—Capsules

One thousand two-piece hard gelatin capsules for oral use, each containing 250 mg of U-57,930E or U-60,970E, are prepared from the following types and amounts of materials:
U-57,930E or U-60,970E: 250 gm
Corn starch: 100 gm
Talc: 75 gm
Magnesium stearate: 25 gm The materials are thoroughly mixed and then encapsulated in the usual manner.

The foregoing capsules are useful for the systemic treatment of infection in adult humans by oral administration of one capsule every 6 hours.

Using the procedure above, capsules are similarly prepared containing U-57,930E or U-60,970E in 10, 25, 50, 100, and 500 mg amounts by substituting 10, 25, 50, 100 and 500 gm of U-57,930E or U-60,970E for the 250 gm used above.

Composition Example 2—Capsules

One thousand two-piece hard gelatin capsules for oral use, each containing 200 mg of U-57,930E or U-60,970E and 250 mg of tetracycline hydrochloride, are prepared from the following types and amounts of ingredients:
U-57,930E or U-60,970E: 200 gm
Tetracycline hydrochloride: 250 gm
Talc: 75 gm
Magnesium stearate: 25 gm The ingredients are thoroughly mixed and then encapsulated in the usual manner.

The foregoing capsules are useful for the systemic treatment of infection in adult humans by the oral administration of one capsule every 6 hours.

Using the procedure above, capsules are similarly prepared containing U-57,930E or U-60,970E and each of the following antibiotics in place of tetracycline by substituting 250 gm of such other antibiotic for tetracycline: chloramphenicol, oxytetracyline, chlortetracycline, fumagillin, erythromycin, streptomycin, dihydronovobiocin and novobiocin. When a penicillin, such as potassium penicillin G, is to be used in place of tetracycline, 250,000 units per capsule is employed.

Such combination products are useful for the systemic treatment of mixed infections in adult humans by the oral administration of one capsule every 6 hours.

Composition Example 3—Tablets

One thousand tablets for oral use, each containing 500 mg of U-57,930E or U-60,970E, are prepared from the following types and amounts of materials:
U-57,930E or U-60,970E: 500 gm
Lactose: 125 gm
Corn starch: 65 gm
Magnesium stearate: 25 gm
Light liquid petroleum: 3 gm The ingredients are thoroughly mixed and slugged. The slugs are broken down by forcing through a number 16 screen. The resulting granules are then compressed into tablets, each tablet containing 500 mg of U-57,930E or U-60,970E.

The foregoing tablets are useful for systemic treatment of infections in adult humans by oral administration of one tablet three times a day.

Using the above procedure, except for reducing the amount of U-57,930E or U-60,970E to 250 gm, tablets containing 250 mg of U-57,930E or U-60,970E are prepared.

Composition Example 4—Tablets

One thousand oral tablets, each containing 250 mg of U-57,930E or U-60,970E and total of 250 mg (83.3 mg each) of sulfadiazine, sulfamerazine, and sulfamethazine, are prepared from the following types and amounts of materials:
U-57,930E or U-60,970E: 250 gm
Sulfadiazine: 83.3 gm
Sulfamerazine: 83.3 gm
Sulfamethazine: 83.3 gm
Lactose: 50 gm
Corn starch: 50 gm
Calcium stearate: 25 gm
Light liquid petrolatum: 5 gm The ingredients are thoroughly mixed and slugged. The slugs are broken down by forcing through a number sixteen screen. The resulting granules are then compressed into tablets, each containing 250 mg of U-57,930E or U-60,970E and a total of 250 mg (83.3 mg each) of sulfadiazine, sulfamerazine, and sulfamethazine.

The foregoing tablets are useful for systemic treatment of infections by the oral administration of four tablets first and then one every six hours.

For the treatment of urinary infections, the triple sulfas in the above formulation is advantageously replaced by 250 gm of sulfamethylthiadiazole or 250 gm of sulfacetamide.

Composition Example 5—Oral Syrup

One thousand cc of an aqueous suspension for oral use, containing in each 5 cc dose 250 mg of U-57,930E or U-60,970E and 500 mg of total sulfas is prepared from the following types and amounts of ingredients:
U-57,930E of U-60,970E: 50 gm
Sulfadiazine: 33.3 gm
Sulfamerazine: 33.3 gm
Sulfamethazine: 33.3 gm
Citric acid: 2 gm
Benzoic acid: 1 gm
Sucrose: 700 gm
Tragacanth: 5 gm
Lemon oil: 2 cc
Deionized water, q.s.: 1000 cc The citric acid, benzoic acid, sucrose, tragacanth, and lemon oil are dispersed in sufficient water to make 850 cc of solution. The U-57,930E or U-60,970E and finely divided sulfas are stirred into the syrup until uniformly distributed. Sufficient water is added to make 1000 cc.

The composition so prepared is useful in the systemic treatment of pneumonia in adult humans at a dose of 1 tablespoonful (10 cc) 4 times a day.

Composition Example 6—Parenteral Solution

A sterile aqueous solution for intramuscular use, containing 200 mg of U-57,930E or U-60,970E in 1 cc is prepared from the following types and amounts of materials:
U-57,930E or U-60,970E: 200 gm
Lidocaine hydrochloride: 4 gm
Methylparaben: 2.5 gm
Propylparaben: 0.17 gm
Water for injection, q.s.: 1,000 cc The ingredients are dissolved in the water and the solution sterilized by filtration. The sterile solution is filled into vials and the vials sealed.

Composition Example 7—Parenteral Preparation

A sterile aqueous composition for intramuscular use, containing in 1 cc 200 mg of U-57,930E or U-60,970E and 400 mg of spectinomycin sulfate is prepared from the following types and amounts of ingredients:
U-57,930E or U-60,970E: 200 gm
Spectinomycin sulfate: 400 gm
Lactose: 50 gm
Water for injection, q.s.: 1,000 cc The U-57,930E or U-60,970E, spectinomycin sulfate, and lactose are dispersed in the water and sterilized. The sterile composition, in the amount of 2 cc. is filled aseptically into sterile vials.

Composition Example 8—Topical Ointment

One thousand gm of 0.25% ointment is prepared from the following types and amounts of ingredients:
U-57,930E or U-60,970E: 2.5 gm
Zinc oxide: 50 gm
Calamine: 50 gm
Liquid petrolatum (heavy): 250 gm
Wool fat: 200 gm
White petrolatum, q.s.: 1,000 gm The white petrolatum and wool fat are melted and 100 gm of liquid petrolatum added thereto. The U-57,930E or U-60,970E, zinc oxide and calamine are added to the remaining liquid petrolatum and the mixture milled until the powders are finely divided and uniformly dispersed. The powder mixture is stirred into the white petrolatum mixture and stirring continued until the ointment congeals.

The foregoing ointment is usefully applied topically to the skin of mammals for the treatment of infection.

The foregoing composition can be prepared by omitting the zinc oxide and calamine.

Following the procedure above, ointments are similarly prepared containing U-57,930E or U-60,970E in 0.5, 1, 2, and 5% amounts by substituting 5, 10, 20 and 50 gm of U-57,930E or U-60,970E for the 2.5 gm used above.

Composition Example 9—Cream

One thousand gm of a vaginal cream are prepared from the following types and amounts of ingredients:
U-57,930E or U-60,970E: 50 gm
Tegacid Regular[1]: 150 gm
Spermaceti: 100 gm
Propylene glycol: 50 gm
Polysorbate 80: 5 gm
Methylparaben: 1 gm
Deionized water, q.s.: 1,000 gm
[1]Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm of water and the propylene glycol, Polysorbate 80, and U-57,930E or U-60,970E are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by incorporating 2.5 gm of citric acid and 0.2 g of dibasic sodium phosphate dissolved in about 50 gm of water. Finally, sufficient water is added to bring the final weight to 1,000 gm and the preparation stirred to maintain homogeneity until cooled and congealed.

The foregoing composition is useful for the treatment of vaginal infections in humans.

Composition Example 10—Ointment, Ophthalmic

One thousand gm of an ophthalmic ointment containing 0.5% U-57,930E or U-60,970E are prepared from the following types and amounts of ingredients:
U-57,930E or U-60,970E: 5 L gm
Bacitracin: 12.2 gm
Polymyxin B sulfate (10,000 units/mg: 1 gm
Light liquid petrolatum: 250 gm
Wool fat: 200 gm
White petrolatum, q.s.: 1,000 gm The solid ingredients are finely divided by means of an air micronizer and added to the ligh liquid petrolatum. The mixture is passed through a colloid mill to uniformly distribute the micronized particles. The wool fat and white petrolatum are melted together, strained, and the temperature adjusted to 45°–50° C. The liquid petrolatum slurry is added and the ointment stirred until congealed. Suitably the ointment is packaged in one dram ophthalmic tubes.

The foregoing ointment is usefully applied to the eye for treatment of localized infection in humans and other animals.

Advantageously the foregoing composition can contain 5 gm (0.5%) of methylprednisolone for the treatment of inflammation, and, alternatively, the bacitracin and polymyxin B sulfate can be omitted.

Composition Example 11—Eye-Ear Drops

One thousand cc of a sterile aqueous solution for eye or ear use containing 10 mg of U-57,930E or U-60,970E and 5 mg of methylprednisolone in each cc is prepared from the following types and amounts of ingredients:
U-57,930E or U-60,970E: 10 gm
Methylprednisolone phosphate sodium: 5 gm
Sodium citrate: 4.5 gm
Sodium bisulfite: 1 gm
Polyethylene glycol 4000: 120 gm
Myristyl-γ-picolinium chloride: 0.2 gm
Polyvinylpyrrolidone: 1 gm
Deionized water, q.s. ad: 1000 cc The ingredients are dissolved in the water and the resulting solution is sterilized by filtration. The solution is aseptically filled into sterile dropper containers.

The composition so prepared is useful in the topical treatment of inflammation and infection of the eye and ear as well as other sensitive tissues of the animal body.

Composition Example 12—Troches

Ten thousand troches are prepared from the following types and amounts of ingredients:
U-57,930E or U-60,970E: 100 gm
Neomycin sulfate: 50 gm
polymyxin B sulfate (10,000 units/mg): 1 gm
Ethyl aminobenzoate: 50 gm
Calcium stearate: 150 gm
Powdered sucrose, q.s.: 5,000 gm The powdered materials are mixed thoroughly and then compressed into half gram troches following the usual techniques for the preparation of compressed tablets.

The troches are held in the mouth and allowed to dissolve slowly to provide treatment for the mouth and throat of humans.

Composition Example 13—Suppository, Rectal

One thousand suppositories, each weighing 2.5 gm and containing 100 mg of U-57,930E or U-60,970E are prepared from the following types and amounts of ingredients:
U-57,930E or U-60,970E: 100 gm
Polymyxin B sulfate (10,000 units/mg): 1.25 gm
Methylprednisolone: 1 gm
Ethyl aminobenzoate: 75 gm
Zinc oxide: 62.5 gm Propylene glycol: 162.5 gm
Polyethylene glycol 4,000 q.s.: 2,500 gm The U-57,930E or U-60,970E, polymyxin B sulfate, methylprednisolone, ethyl aminobenzoate, and zinc oxide are added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C.

The composition is allowed to cool and solidify and then removed from the mold and each suppository foil wrapped.

The foregoing suppositories are inserted rectally for local treatment of inflammation and infection.

Alternatively, the foregoing composition can be prepared omitting the steroid.

Composition Example 14—Mastitis Ointment

One thousand gm of an ointment for the treatment of mastitis in dairy cattle is prepared from the following types and amounts of ingredients:
U-57,930E or U-60,970E: 25 gm
Methylprednisolone acetate: 0.5 gm
Light liquid petrolatum: 300 gm
Chlorobutanol, anhydrous: 5 gm
Polysorbate 80: 5 gm
2% Aluminum monostearate-peanut oil gel: 400 gm
White petrolatum, q.s.: 1000 gm The U-57,930E or U-60,970E and methylprednisolone acetate are milled with the light liquid petrolatum until finely divided and uniformly dispersed. The chlorobutanol, polysorbate 80, peanut oil gel and white petrolatum are heated to 120° F. to form a melt and the liquid petrolatum dispersion stirred in. With continued stirring, the dispersion is allowed to cool (and congeal) to room temperature and is filled into disposable mastitis syringes in 10 gm doses.

Composition Example 15—Animal Feed

One thousand gm of a feed mix is prepared from the following types and amounts of ingredients:
U-57,930E or U-60,970E: 10 gm
Soybean meal: 400 gm
Fish meal: 400 gm
Wheat germ oil: 50 gm
Sorghum molasses: 140 gm The ingredients are mixed together and pressed into pellets. The composition can be fed to laboratory animals, i.e., rats, mice, guinea pigs, and hamsters for prophylaxis during shipping.

For other animals such as poultry, e.g., chickens, ducks, turkeys, and geese, the composition can be added to the animal's regular feed in an amount calculated to give the desired dose of U-57,930E or U-60,970E.

Composition Example 16

Following the procedure of each of the preceding Composition Examples 1-15, inclusive, each antibacterially-active compound of the subject invention is substituted in an equivalent amount for the U-57,930E or U-60,970E shown in the example to provide therapeutic properties.

Similarly, each of the above free base compounds can be used in the form of a pharmaceutically (or pharmacologically) acceptable salt, e.g., hydrochloride, sulfate, phosphoric, sodium, potassium, calcium, and lithium.

CHART 1

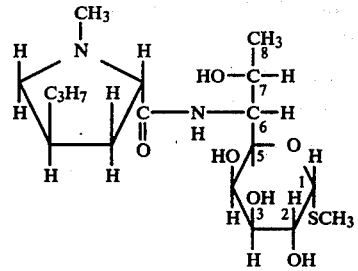

(1)

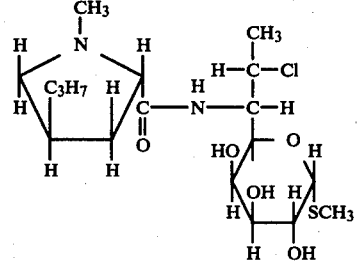

(2)

CHART 2

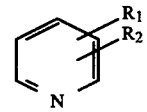

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxy-methyl 1-thio-α-lincosaminide, 7-deoxy-7(S)-(methylthio)-methyl 1-thio-α-lincosaminide, 7-deoxy-7(S)-(2-hydroxyethylthio)-methyl 1-thio-α-lincosaminide and 7-deoxy-7(S)-(3-hydroxypropylthio)-methyl 1-thio-α-lincosaminide; and the pharmaceutically acceptable salts thereof.

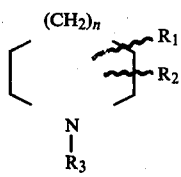

wherein $R_1$ and $R_2$, which can be in the 2, 3, 4, 5, 6, 7, 8, or 9 position of the ring, are as defined above; wherein $R_3$ is selected from the group consisting of H, $CH_3$, $C_2H_5$, and $-CH_2-CH_2-OH$; wherein n is an integer of from 1 to 4, inclusive; and the pharmaceutically acceptable salts thereof.

wherein A, B and E are selected from the group consisting of nitrogen, oxygen, sulfur and $CR_1R_1$; $R_1$ and $R_2$ are as defined above, and can be attached to any ring carbon or nitrogen atom; $R_1$ can be multiply attached to any ring carbon atom; and the pharmaceutically acceptable salts thereof.

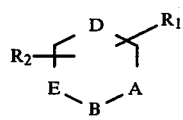

wherein A, B, D and E are selected from the group consisting of nitrogen, oxygen, sulfur and $CR_1R_1$; $R_1$ and $R_2$ are as defined above and can be attached to any ring carbon or nitrogen atom; $R_1$ can be multiply attached to any ring carbon atom, and the pharmaceutically acceptable salts thereof.

CHART 3

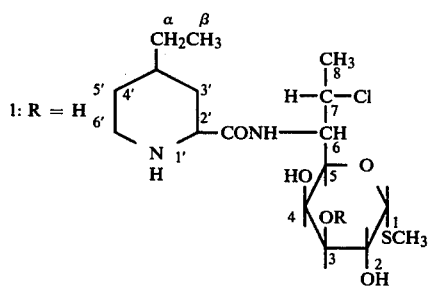

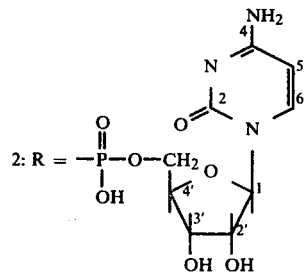

-continued
CHART 3

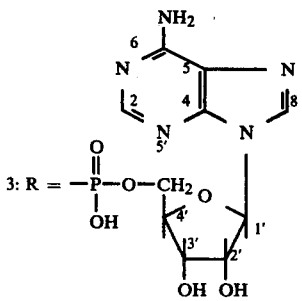

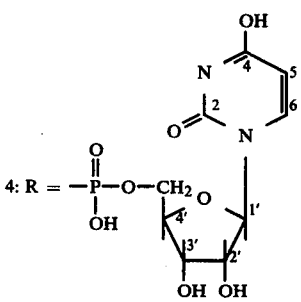

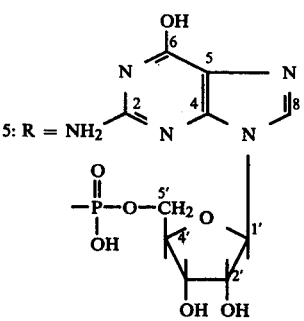

1: U-57930
2: U-57930 3-(5'-cytidylate)
3: U-57930 3-(5'-adenylate)
4: U-57930 3-(5'-uridylate)
5: U-57930 3-(5'-guanylate)

We claim:
1. The 3-(5'-ribonucleotide) of a compound having the formula

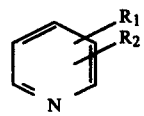

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl of from 3 to 8 carbon atoms inclusive, substituted oxygen, substituted nitrogen, halogen, phenyl, and substituted phenyl, $-(CH_2)_n-OH$, $-(CH_2)_n-NR_4R_5$, and branched chain isomers thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosaminide; and the pharmaceutically acceptable salts thereof.

2. The 3-(5'-ribonucleotide) of a compound having the formula

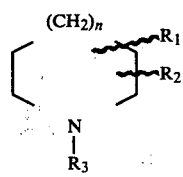

wherein $R_1$ and $R_2$, which can be in the 2, 3, 4, 5, 6, 7, 8, or 9 position of the ring, are as defined in claim 1; wherein $R_3$ is selected from the group consisting of H, $CH_3$, $C_2H_5$, and $-CH_2-CH_2-OH$; wherein n is an integer of from 1 to 4, inclusive; and the pharmaceutically acceptable salts thereof.

3. A compound, as defined in claim 1, wherein $R_1$ is in the 4 position and is alkyl of from 1 to 8 carbon atoms, inclusive, and isomeric forms thereof; wherein $R_2$ is in the 2 or 3 position; and the pharmaceutically acceptable salts thereof.

4. A compound, as defined in claim 2, wherein $R_1$ is in the 4 position and is alkyl of from 1 to 8 carbon atoms, inclusive, and isomeric forms thereof, and the pharmaceutically acceptable salts thereof.

5. The 3-(5'-ribonucleotide) of a compound having the formula

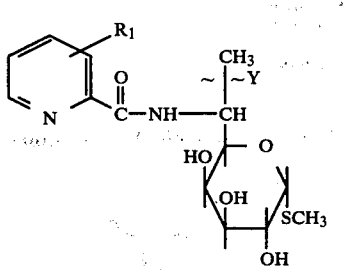

wherein $R_1$, which can be singly or multiply substituted in the 3, 4, 5, or 6 position of the pyridine ring, is selected from the group consisting of hydrogen, alkyl and substituted alkyl wherein the alkyl portion is from 1 to 8 carbon atoms, inclusive, and isomeric forms thereof, cycloalkyl of from 3 to 8 carbon atoms, inclusive and substituted cycloalkyl, substituted oxygen, substituted nitrogen, halogen, phenyl, and substituted phenyl, $-(CH_2)_n-OH$, $-(CH_2)_n-NR_4R_5$, and branched chain isomers thereof, wherein n is an integer of from 1 to 8, inclusive, $R_4$ and $R_5$ are H or alkyl of from 1 to 8 carbon atoms, inclusive, and isomeric forms thereof; wherein Y is selected from the group consisting of 7(S)-halo and 7(R)-halo; and the pharmaceutically acceptable salts thereof.

6. A compound, as defined in claim 5, wherein Y is 7(S)-halo, and the pharmaceutically acceptable salts thereof.

7. The 3-(5'-ribonucleotide) of a compound having the formula

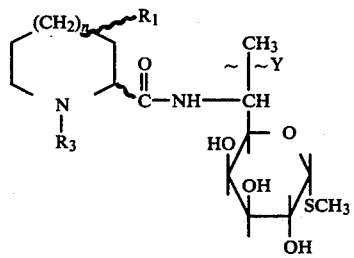

wherein $R_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and isomeric forms thereof, cycloalkyl of from 3 to 8 carbon atoms, inclusive and substituted cycloalkyl, substituted oxygen, substituted nitrogen, halogen, phenyl, and substituted phenyl, $-(CH_2)_n-OH$, $-(CH_2)_n-NR_4R_5$, and branched chain isomers thereof, wherein n is an integer of from 1 to 8, inclusive, $R_4$ and $R_5$ are H or alkyl of from 1 to 8 carbon atoms, inclusive, and isomeric forms thereof; wherein $R_3$ is selected from the group consisting of H, $CH_3$, $C_2H_5$, and $-CH_2-CH_2-OH$; wherein n is an integer of from 1 to 4, inclusive, wherein Y is selected from the group consisting of 7(S)-halo and 7(R)-halo; and the pharmaceutically acceptable salts thereof.

8. A compound, according to claim 7, wherein 7(S)-halo is 7(S)-chloro.

9. A compound, as defined in claim 7, wherein Y is 7(S)-halo; $R_1$ is alkyl of from 1 to 8 carbon atoms, inclusive, and isomeric forms thereof; $R_3$ is hydrogen, and the pharmaceutically acceptable salts thereof.

10. A compound, as defined in claim 9, wherein Y is 7(S)-halo; $R_1$ is $C_2H_5$ and $R_3$ is hydrogen.

11. A compound, as defined in claim 9, wherein Y is 7(S)-halo; $R_1$ is $C_4H_9$ and $R_3$ is hydrogen.

12. A compound, as defined in claim 9, wherein 7(S)-halo is 7(S)-chloro.

13. A compound, as defined in claim 10, wherein 7(S)-halo is 7(S)-7(S)-chloro.

14. A compound, as defined in claim 11, wherein 7(S)-halo is 7(S)-chloro.

15. The 3-(5'-ribonucleotide) of a compound having the formula

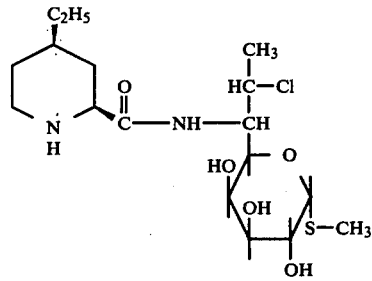

and the pharmaceutically acceptable salts thereof.

16. The 3-(5'-ribonucleotide) of a compound having the formula

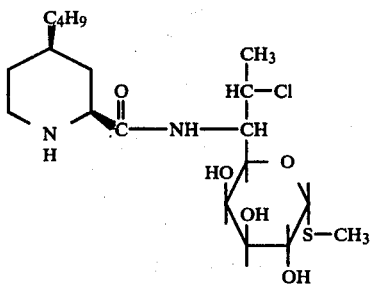

the 2-palmitate; and the pharmaceutically acceptable salts thereof.

17. The 3-(5'-ribonucleotide) of a compound having the formula

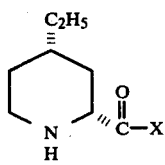

wherein X is selected from the group consisting of 7(S)-halo-methyl 1-thio-α-lincosaminide and 7(R)-halo-methyl 1-thio-α-lincosaminide; and the pharmaceutically acceptable salts thereof.

18. The 3-(5'-ribonucleotide) of a compound having the formula

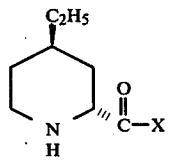

wherein X is as defined in claim 17, and the pharmaceutically acceptable salts thereof.

19. The 3-(5'-ribonucleotide) of a compound of the formula

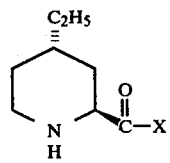

wherein X is as defined in claim 17, and the pharmaceutically acceptable salts thereof.

20. The 3-(5'-ribonucleotide) of a compound having the formula

wherein A, B and E are selected from the group consisting of nitrogen, oxygen, sulfur and $CR_1R_1$; $R_1$ and $R_2$ are as defined in claim 1, and can be attached to any ring carbon or nitrogen atom; $R_1$ can be multiply attached to any ring carbon atom, and the pharmaceutically acceptable salts thereof.

21. The 3-(5'-ribonucleotide) of a compound having the formula

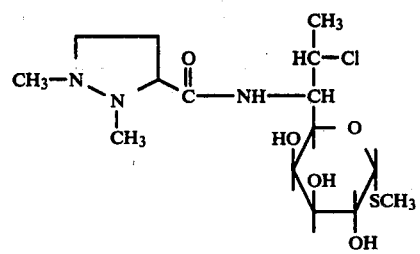

and the pharmaceutically acceptable salts thereof.

22. The 3-(5'-ribonucleotide) of a compound having the formula

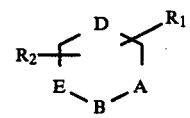

wherein A, B, D and E are selected from the group consisting of nitrogen, oxygen, sulfur and $CR_1R_1$; $R_1$ and $R_2$ are as defined in claim 1, and can be attached to any ring carbon or nitrogen atom; $R_1$ can be multiply attached to any ring carbon atom, and the pharmaceutically acceptable salts thereof.

23. A compound, according to claim 22, wherein said compound can be shown by the formula

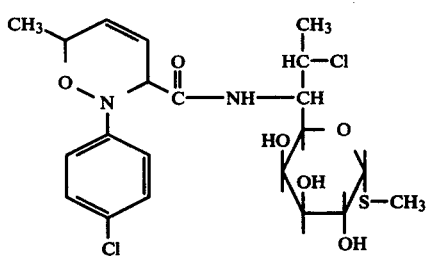

and the pharmaceutically acceptable salts thereof.

24. The 3-(5'-ribonucleotide) of a compound having the formula

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl of from 3 to 8 carbon atoms, inclusive and substituted cycloalkyl, substituted oxygen, substituted nitrogen, halogen, phenyl, and substituted phenyl, —$(CH_2)_n$—OH, —$(CH_2)_n$—$NR_4R_5$, and branched chain isomers thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosaminide; and the pharmaceutically acceptable salts thereof.

25. The 3-(5'-ribonucleotide) of a compound having the formula

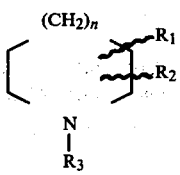

wherein $R_1$ and $R_2$, which can be in the 2, 3, 4, 5, 6, 7, 8, or 9 position of the ring, are as defined in claim 1; wherein $R_3$ is selected from the group consisting of H, $CH_3$, $C_2H_5$, and $-CH_2-CH_2-OH$; wherein n is an integer of from 1 to 4, inclusive; and the pharmaceutically acceptable salts thereof.

26. A compound of the formula

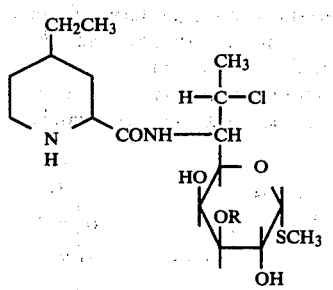

wherein R is

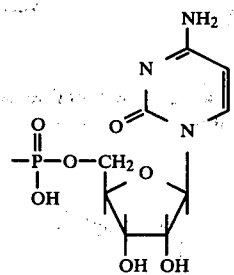

27. A compound of the formula

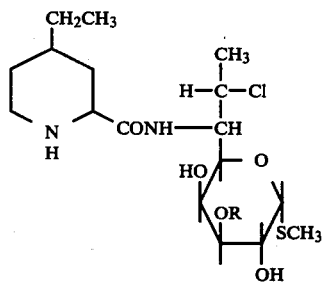

wherein R is

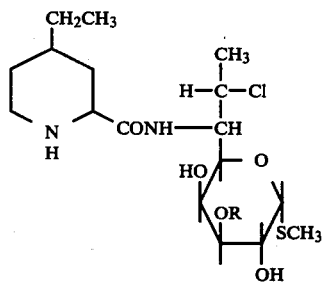

28. A compound of the formula

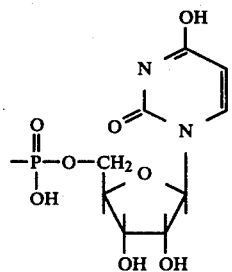

wherein R is

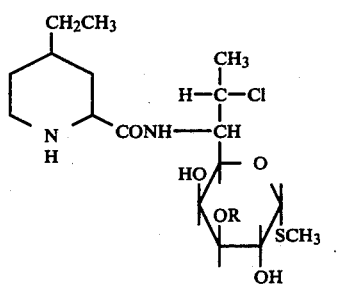

29. A compound of the formula

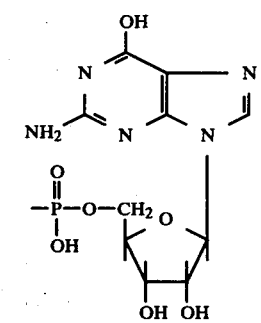

wherein R is

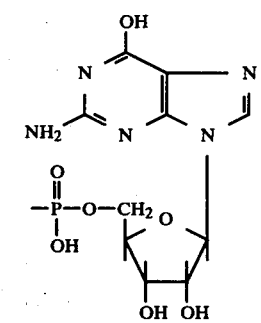

* * * * *

UNITED STATES PATENT OFFICE
CERTIFICATE OF CORRECTION

Patent No. 4,383,109　　　　　　　　Dated May 10, 1983

Inventor(s) A.D. Argoudelis, D.W. Stroman

It is certified that error appears in the above-identified patent and that said Letters Patent are hereby corrected as shown below:

Column 3, line 20, "After the twelve" should read --After twelve--
Column 3, line 23, "the HU-57930" should read --the U-57930
Column 7, line 52, "of essentially" should read --of Essentially--
Column 16, line 63, "quantities or the active" should read --quantities of the active--
Column 17, line 58, "depending on the form and concentrated used," should read --depending on the form and concentration used,--
Column 18, lines 46, 47, "U-58,930E or U-60,970E" should read --U-57,930E or U-60,970E--
Column 19, line 46, "Light liquid petroleum" should read --Light liquid petrolatum--
Column 21, line 67, "U-60,970E: 5 L gm" should read --U-60,970E: 5 gm--
Column 26, Claim 1, lines 61-63, "cycloalkyl and substituted cycloalkyl of from 3 to 8 carbon atoms inclusive" should read --cycloalkyl of from 3 to 8 carbon atoms, inclusive and substituted cycloalkyl,--

Signed and Sealed this

Twelfth Day of July 1983

[SEAL]

Attest:

GERALD J. MOSSINGHOFF

Attesting Officer　　Commissioner of Patents and Trademarks